United States Patent [19]

Kulwiec et al.

[11] Patent Number: 4,483,677
[45] Date of Patent: * Nov. 20, 1984

[54] FLEXIBLE CLASP FOR A REMOVABLE PARTIAL DENTAL PROSTHESIS AND METHOD OF FORMATION OF A COMBINED FLEXIBLE CLASP AND STRESS RELIEVING PROSTHESIS

[76] Inventors: Leonard J. Kulwiec, 2103 Lark Glen, Excondido, Calif. 92026; Michael F. X. Kulwiec, 816 Piner Rd., Santa Rosa, Calif. 95401

[ * ] Notice: The portion of the term of this patent subsequent to Nov. 1, 2000 has been disclaimed.

[21] Appl. No.: 521,699

[22] Filed: Aug. 10, 1983

Related U.S. Application Data

[63] Continuation-in-part of Ser. No. 303,560, Sep. 18, 1981, Pat. No. 4,412,824.

[51] Int. Cl.³ ............................................. A61C 13/28
[52] U.S. Cl. .................................................. 433/170
[58] Field of Search ............................... 433/169, 170

[56] References Cited

U.S. PATENT DOCUMENTS 2,674,040  4/1954  Lenzer .................................. 433/170

Primary Examiner—Robert Peshock
Attorney, Agent, or Firm—Manfred M. Warren; Robert B. Chickering; Glen R. Grunewald

[57] ABSTRACT

A flexible clasp for removable mounting of a partial dental prosthesis to an abutment tooth is disclosed. The clasp includes a retention arm (42) formed to extend around at least a portion of the side of an abutment tooth (27) to retain the prosthesis in an edentulous space (26). In the improved clasp (41), the retention arm (42) is coupled to the prosthesis at a location in the edentulous space, preferably about one tooth width from abutment tooth (27) so as to cantilever support the retention arm (42) for resilient lateral displacement with respect to the abutment tooth. Preferably, a resiliently displaceable tubular member (51) is mounted to the retention arm (42) which is held to the prosthesis by a clip (43) surrounding the tubular member (51) and arm (42). The method of the present invention includes coupling the prosthesis to the clasp (41) through the retention arm portion (42) of the clasp while maintaining the resilient displaceability of the retention arm (42) to provide both a retention function and a stress relieving function.

10 Claims, 6 Drawing Figures

U.S. Patent  Nov. 20, 1984  4,483,677

FLEXIBLE CLASP FOR A REMOVABLE PARTIAL DENTAL PROSTHESIS AND METHOD OF FORMATION OF A COMBINED FLEXIBLE CLASP AND STRESS RELIEVING PROSTHESIS

RELATED APPLICATION

This application is a continuation-in-part application based upon prior pending Application Ser. No. 303,560, filed Sept. 18, 1981 for "REMOVABLE PARTIAL DENTAL PROSTHESIS AND METHOD OF FORMING AND SUPPORTING THE SAME and now U.S. Pat. No. 4,412,824 issued Nov. 1, 1983."

BACKGROUND OF THE INVENTION

Considerable work has been undertaken in connection with providing a connection or coupling between a removable partial dental prosthesis and the abutment tooth or teeth defining an edentulous space in which the prosthesis is to be retained. It is generally recognized in the literature that if the stress on a partial denture is passed or transmitted directly to the abutment tooth, the stress will break down the periodontal fibers supporting the abutment tooth, with resultant eventual loss of the tooth. In order to avoid this problem, various means for connecting partial dental prosthesis to an abutment tooth have been developed, including the devices set forth in U.S. Pat. Nos. 4,293,303, 3,412,468 and 1,545,734. Additional stress relieving connections are disclosed in Italian Patent Nos. 541,013, 502,531 and 489,861.

In our prior above-identified patent application, a removable partial dental prosthesis is disclosed in which the connection between the prosthesis and the abutment tooth is provided by a cantilevered arm structure. The connection includes a resilient element which enables limited universal linear and articulated movement of the prosthesis with respect to the abutment tooth so as to reduce the stress passed through the connection to the abutment tooth and the periodontal fibers. In this prior dental prosthesis, the prosthesis is coupled to the abutment tooth by a standard dental clasp. The function of the dental clasp is to retain the prosthesis in the edentulous space by resilient lateral engagement with the sides of the abutment tooth to prevent the denture from slipping vertically over the abutment tooth under the action of gravity and/or sticky food.

A clasp for a partial dental prosthesis typically includes a retention arm which is cantilevered from the edentulous side of the abutment tooth and passes around and encircles part of the tooth. The retention arm is resiliently flexible so as to grip the tooth and retain the prosthesis against removal. The retention arm, however, must also be flexible enough to enable the wearer to pull the clasp over the abutment tooth for removal of the prosthesis.

A prosthodontist conventionally employs a device called a parallelometer or surveyor to determine and trace the parallel line around the greatest circumference of the abutment tooth in a horizontal plane. This line is called the "survey line," and the area below the survey line is the undercut area, with the area above being the bracing or stabilizing area. Typically, the retention arm of a standard clasp encircles the abutment tooth with its upper edge above or extending along the survey line and the lower edge and free end of the arm below the survey line.

Retention arms are usually generally semicircular in cross-section with the flat side of the semicircle engaging the tooth surface, and are cantilevered from a vertically extending post portion of the clasp which is positioned next to the edentulous space. Standard clasps also typically include a rest or horizontally extending protrusion from the top of the vertical post which engages the top of the tooth and limits vertical displacement toward the gum line. Most clasps also include a second or reciprocal arm or band which is cantilevered from the post on an opposite side of the abutment tooth from the retention arm.

In operation, a conventional clasp flexes laterally with respect to the surface of the abutment tooth as it passes over the survey line and resiliently springs back against the tooth once in the undercut area to frictionally retain the denture in the edentulous space.

As above set forth, the improved dental prosthesis of our prior application involves the positioning of a universally displaceable connection between the standard dental clasp and the prosthesis. The present invention relates to an improvement in the clasp itself and thereby to an improvement in the connection between the prosthesis and the clasp.

One of the problems which is prevalent in a conventional dental clasps for a removable partial prosthesis is that the lateral resiliency inherent in the cantilevered retention arm is relatively limited. In the clasp structure, the distance to the free end of the retention arm from the vertical post portion of the clasp is very small. Accordingly, it is not possible to build in very much resiliency, and attempts to enhance this resiliency have been largely directed toward flattening the retention arm cross-section so as to make it somewhat more flexible. An additional advantage of such flattening is that more of the abutment tooth will be engaged by the band, which enhances the frictional retentive effect of the clasp.

A disadvantage of such clasp constructions, however, is that because of the lack of resiliency, the band must be placed fairly close to the survey line or relatively high on the abutment tooth. This means that the retention arm band will often be quite visible and cosmetically objectionable to the wearer. The result is often that the user of the dental prosthesis does not wear the same as often as would otherwise be desirable.

Another disadvantage of prior flexible clasp constructions for partial dental prosthesis has been that it is difficult to generate enough retention force in the clasp to withstand the forces tending to pull the clasp off of the abutment tooth because the limited flexibility does not permit engagement of the abutment tooth to any substantial degree in the undercut area. Accordingly, mastication of sticky foods can be particularly troublesome with respect to the retention of removal of partial prosthesis in the upper jaw.

OBJECTS OF THE INVENTION

Accordingly, it is an object of the present invention to provide a flexible clasp for a removable partial dental prosthesis which is constructed so as to improve the retention of the prosthesis on the abutment tooth and yet permit easy removal when required.

Another object of the present invention is to provide a clasp for a removable partial dental prosthesis which is cosmetically more pleasing and can engage less surface area on the abutment tooth at a position closer to the gum line.

Still a further object of the present invention is to provide a flexible clasp for a removable dental prosthesis which can also be combined to provide a stress relieving connection between the abutment tooth and the prosthesis.

Still a further object of the present invention is to provide a flexible clasp for removable dental prosthesis which is easy to manufacture, durable, and can be readily cleaned, maintained and repaired.

Another object of the present invention is to provide a method for forming a stress relieving removable partial dental prosthesis in which lateral flexibility in the clasp portion of the prosthesis is also employed to effect a flexible connection between the prosthesis and the abutment tooth.

Still a further object of the present invention is to provide a method for forming a resiliently displaceable clasp for a removal dental prosthesis in which flexibility in the connection between the prosthesis and the clasp is employed to provide lateral resiliency for retention of the clasp on the abutment tooth.

The flexible clasp for a removable partial dental prosthesis and the method of forming the combined clasp and prosthesis have other objects and features of advantage which will become apparent from and are set forth in the accompanying drawing and the following description of the preferred embodiment.

SUMMARY OF THE INVENTION

The flexible clasp for retaining a removable partial dental prosthesis of the present invention includes retention means, such as an arm, which is formed to engage and extend around a portion of the side of the abutment tooth and which is formed to be resiliently laterally displaceable with respect to the abutment tooth. In one aspect, the improvement in the clasp of the present invention is comprised of the retention means being formed as an arm which is coupled to the prosthesis at a location in the edentulous space about one tooth width from the abutment tooth with the arm being cantilevered from the prosthesis in the edentulous space and extending from the prosthesis around and engaging a side of the tooth to provide enhanced lateral resilient displacement in the clasp. In another aspect of the present invention, the retention means is formed as an arm which extends around a side of the tooth and a resiliently displaceable element is mounted to the arm for cooperation with the arm to provide lateral displacement for retention and displacement for stress relieving connection between the prosthesis and the abutment tooth.

The method of the present invention includes the step of flexibly connecting a dental prosthesis to clasp means formed for resilient lateral displacement of a retention portion thereof. In the improvement of the present method, the flexible connecting step is accomplished by coupling the prosthesis to clasp means through the retention portion while maintaining resilient displacement of the retention portion to provide both a retention function and a stress relieving function.

DESCRIPTION OF THE PREFERRED EMBODIMENT

Figure 1:
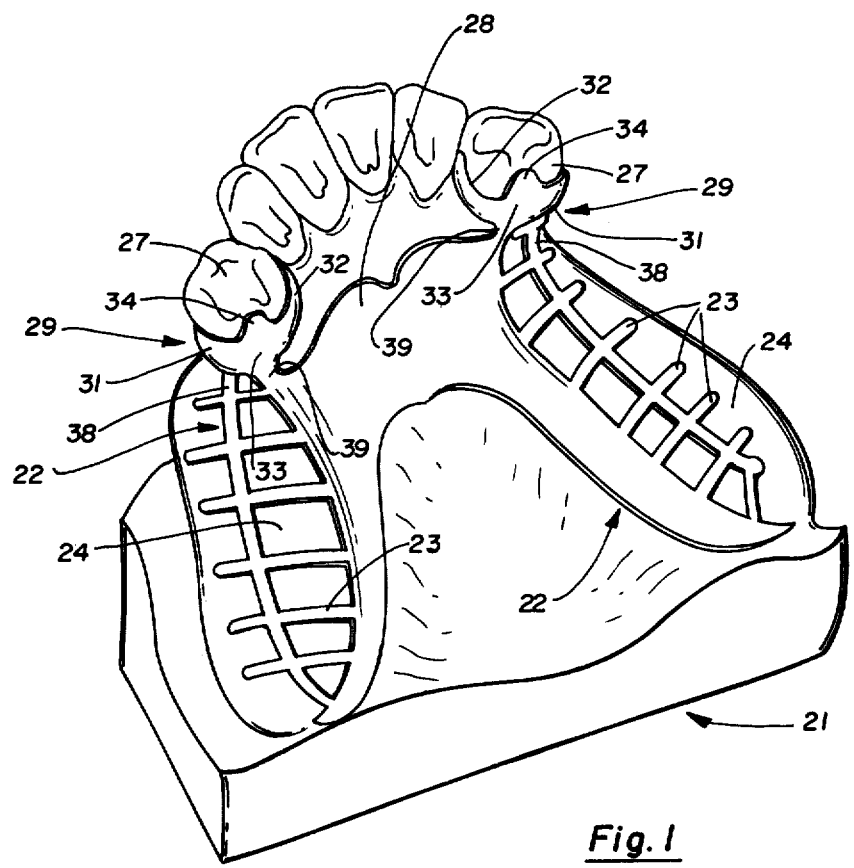
FIG. 1 is a top perspective view of an upper dental arch showing the base of a dental prosthesis mounted thereto with conventional clasps.
Figure 2:
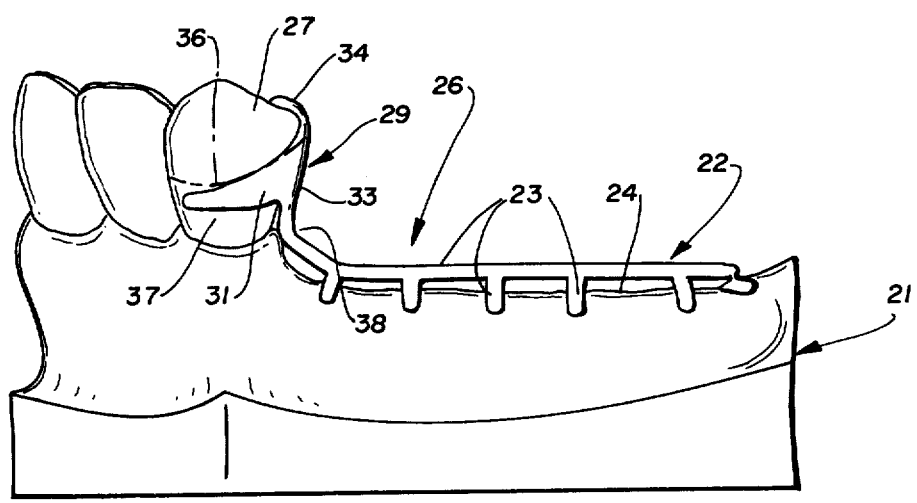
FIG. 2 is a side elevational view of the dental arch of FIG. 1.

Referring now to FIGS. 1 and 2, a master model, generally designated 21, for an upper dental arch is shown with base means, generally designated 22, for a dental prosthesis mounted thereon. Base 22 is preferable formed with webbings 23 which are formed and positioned to mate with alveolar ridges 24 in the edentulous spaces 26 rearwardly of abutment teeth 27. As shown in the drawing, the prosthesis is designed for positioning on alveolar ridges 24 on both sides of the dental arch, and base means 22 preferably includes a major connector (palatal horseshoe) 28 which joins webbings 23 on each side of the dental arch together as a unit. As will be understood, however, the clasp and prosthetic of the present invention are suitable for use with a removable partial prosthesis designed to be placed on only one side of the dental arch.

As shown in FIGS. 1 and 2, standard clasps, generally designated 29, have been cast as part of the base 22 and extend around the abutment teeth 27 on either side of the dental arch. Each of clasps 29 includes a retention arm 31 (best seen in FIG. 2), and a reciprocal arm 32 mounted to a vertically extending post, shoulder or minor connector 33 in order to limit the displacement of the prosthesis toward the gums. It is further preferable that clasps 29 include a rest portion 34 which engages a horizontally extending or top surface of abutment tooth 27.

As thus far described, the prosthetic device is constructed in a manner well known in the prior art for removable partial denture prosthetics. As best may be seen in FIG. 2, retention arm 31 is formed to extend down below survey line 36 (shown in phantom) on abutment tooth 27 so that the arm 31 is in undercut area 37 of the abutment tooth. In order to position retention arm 31 in undercut area 37, however, the retention arm must outwardly flex as it is urged down over abutment tooth 27 to allow it to pass over survey line 36 to the undercut area. Retention arm 31 is advantageously somewhat tapered and semicircular in cross section to enhance flexure with respect to shoulder portion 33 from which the arm is cantilevered.

In our prior Application Ser. No. 303,560, the partial dental prosthetic is connected to clasps 29 by a universally flexible connection coupled to vertically extending shoulder portion 33 of the clasps. Thus, instead of connecting the prosthetic to clasps 29 through metal connectors or neck portions 38 and 39, the only connection between the base 22 and clasp means 29 in our prior application is a universally displaceable coupling having one end mounted to vertical post portion 33 and the other mounted to web portion 23 of the base.

In the improved removal of partial prosthesis of the present invention, clasps 29 have been substantially improved, and their clasping function has been combined with the universal flexible connection to achieve a stress relieving function, as well as a clasping or retentive function.

Figure 3:
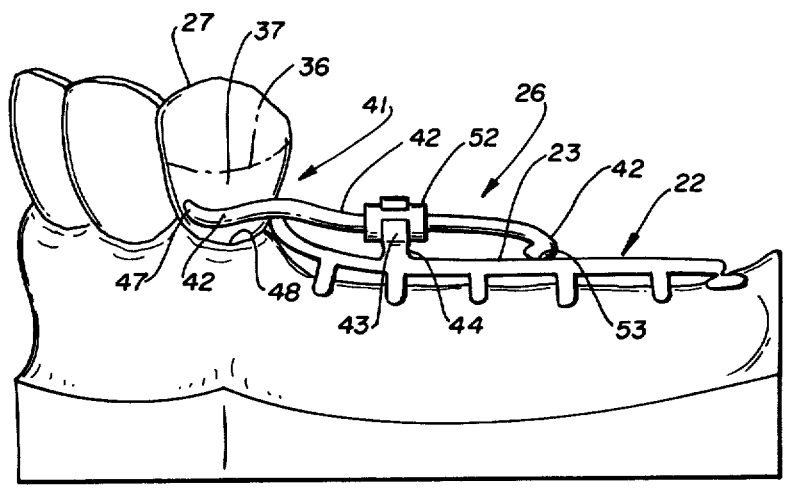
FIG. 3 is a side elevational view corresponding to FIG. 2 and showing an intermediate stage of formation of the flexible clasp of the present invention.
Figure 4:
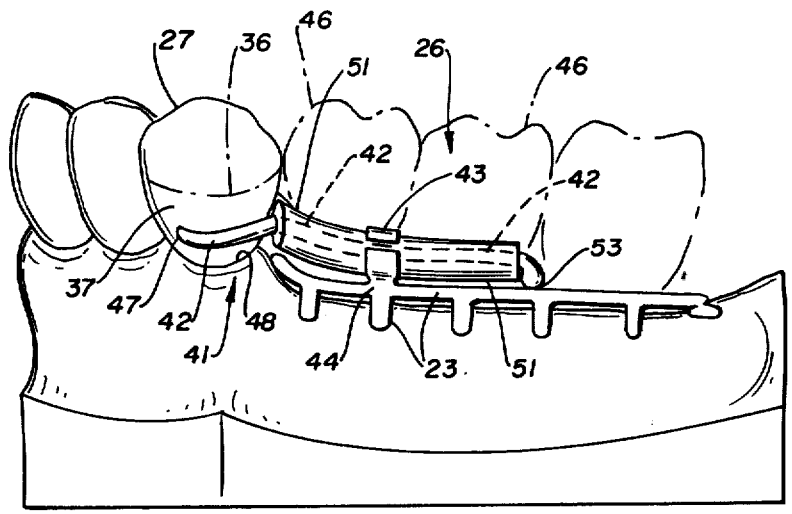
FIG. 4 is a side elevational view corresponding to FIGS. 2 and 3 showing the flexible clasp of the present invention as completely formed and mounted to the base of the prosthesis.
Figure 6:
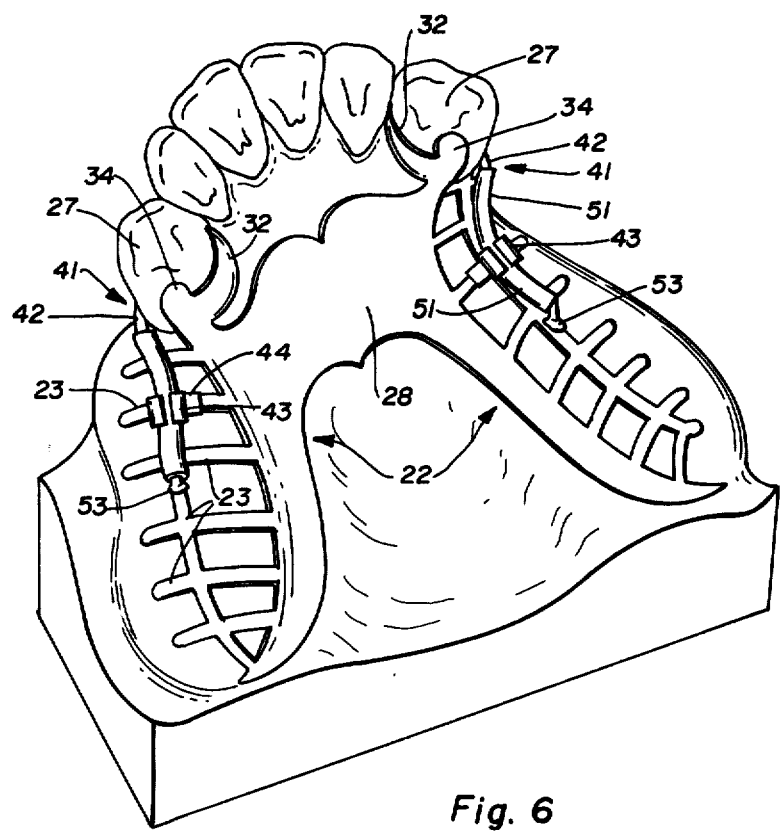
FIG. 6 is a top perspective view corresponding to FIG. 1 and showing the clasp and dental prosthesis constructed in accordance with the present invention.

As best may be seen by reference to FIGS. 3, 4 and 6, a new flexible clasp, generally designated 41, is provided for mounting of a partial dental prosthesis to abutment teeth 27. Clasp 41 includes retention means, preferably in the form of an arm 42, formed to engage and extend around at least a portion of a side of the abutment teeth 27. As is broadly the case with prior art clasp, improved clasp 41 includes an arm 42 which is formed to be laterally flexed to enable the same to pass over survey line 36 into undercut area 37.

In order to provide the necessary lateral flexibility and in fact to enhance the lateral flexibility, the improved clasp of the present invention is constructed so that retention arm 42 is coupled to prosthesis base 22 at a location in edentulous space 26 of about one tooth width from abutment tooth 27 or more. As best may be seen in FIG. 4, arm 42 extends into edentulous space 26 to the location of clip means 43 which is mounted or coupled to webbing 23 by a tang portion 44 fused to the webbing. Clip 44 is shown in FIG. 4 to be positioned in the edentulous space at about the width of one artificial tooth 46 away from abutment tooth 27. Thus, arm 42 is cantilever supported from clip 43, with the length of the arm from the distal end 47 of the arm to clip 43 being substantially longer than the distance from post portion 33 to the distal end of retention arm 31, as described in connection with the clasp of FIG. 2.

Extension of the retention arm 42 into edentulous space 43 so as to enable a longer lever arm, results in a clasp which can be outwardly displaced to a greater distance and still spring back to grasp the abutment tooth. Thus, it is possible with the clasp of the present invention for retention arm 42 to engage abutment tooth 37 at a distance much farther below survey line 36 and only slightly above the level of the gums 48. Additionally, instead of having a relatively thick band, the retention arm of the present invention can be a relatively small diameter circular member. The combination is cosmetically much more appealing, as will be seen by comparing FIGS. 2 an 4.

The clasp of the present invention further preferably includes a standard reciprocal arm 32 and rest 34 which are coupled to major connector portion or palatal horseshoe 28 of the base, although unconfigurations the reciprocal arm and rest may not be required.

Figure 5:
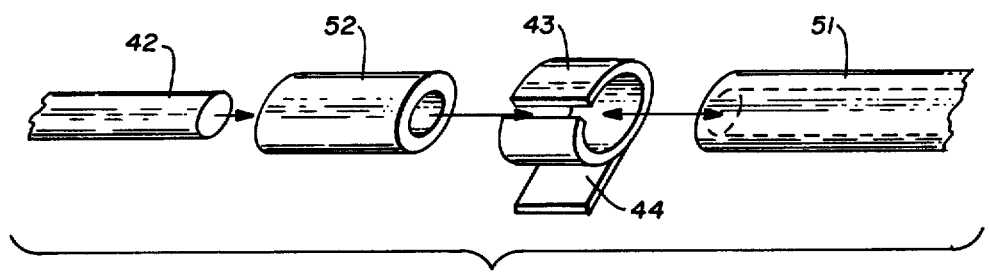
FIG. 5 is an exploded view of the elements to be assembled to form the clasp of the present invention in a stage of its formation shown in FIG. 3.

In order to further enhance the resiliency and lateral deflection of retention arm 42, and further to provide an enhanced universal connection between the prosthesis and the abutment tooth on which it is retained, it it is preferable that the clasp of the present invention include resiliently displaceable coupling means, such as a tubular member 51, mounted concentrically about arm 42 and between arm 42 and clip 43. In a manner similar to the method described in our prior Application Ser. No. 303,560, arm 42 can be mounted by a ceramic spacer 52 in clip 43 (see FIGS. 3 and 5). Arm 42 can then be fused to base 23 at 53, and the spacer broken away by an eccentric burr or other means. A thin film of volcanizing silicone can then be applied to arm 42 and a tubular silicone sleeve or a like compressible drawn over terminal end 47 and through clip 43 to the position shown in FIG. 4. The tube mounted on arm 42 now acts as a flexible connection between abutment tooth 27 to relieve stress and further acts as a resilient laterally flexible mount for the clasp to retain the prosthesis in the edentulous space.

It is an additional important feature of the present invention to be able to employ a retention arm 42 formed with a circular cross-section. Instead of a band-type semicircular arm 31, arm 42 of the clasp of the present invention is preferably circular. This results in a minimum of contact area between abutment tooth 27 and the retention arm, which is permissible in light of the improved lateral flexibility of the tension arm. Additionally, this minimal area and cylindrical contact between the retention arm and abutment tooth minimizes the torque stress passed through the flexible connection to the abutment tooth. Thus, it enhances the stress relieving characteristics of the connection between the prosthesis and the abutment tooth.

The method of the present invention of forming a stress relieving removable partial dental prosthesis includes the step of flexibly connecting a dental prosthesis to clasp means formed for resilient lateral displacement of a retention portion or arm of the clasp means. In the improved method, the flexible connecting step is accomplished by coupling the prosthesis to clasp means 41 through the resiliently displaceable retention portion 42. Thus, in a broad aspect of the present invention, the resilient displaceability heretofore found in clasps has now been employed to couple the prosthesis to the clasp for two functions, namely, retention and stress relieving. A resiliently displaceable element such as tubular member 51 is mounted to arm 42 and the arm and element are formed for cooperative resilient coupling of the arm to the prosthesis to provide both lateral displacement required for mounting and removal of the prosthesis and retention of the same on the abutment tooth, and to provide stress relieving connection between the prosthesis and abutment tooth 27.

As stated conversely, the method of the present invention is a method for forming a resiliently displaceable connection of a removable dental prosthesis to clasp means including the step of connecting the prosthesis to the clasp by a resiliently displaceable connection. The improvement in the connecting step is the step of coupling the prosthesis to a retention portion of the clasp to provide both lateral deflection of the retention portion and stress relieving resilient displacement of the prosthesis. Stated in either manner, clasp 41 provides both an improved clasping structure and a stress relieving connection between the prosthesis and the abutment tooth. This is accomplished by employing the area under the artificial teeth 46 of the prosthesis as an area suitable for construction of not only a connection between the clasp and prosthesis, but a portion of the clasp itself.

What is claimed is:

1. A flexible clasp for removable mounting of a partial dental prosthesis to an abutment tooth, said clasp being coupled to said prosthesis and including retention means formed to engage and extend around at least a portion of the side of said abutment tooth to retain said prosthesis in an edentulous space proximate said abutment tooth, said retention means being further formed to be resiliently laterally displaceable with respect to said side of said abutment tooth during mounting of said prosthesis to and removal from said edentulous space, wherein the improvement in said clasp is comprised of:

said retention means being formed as an arm coupled to said prosthesis at a location in said edentulous space at least about one tooth width from said abutment tooth, said arm being cantilever supported from said prosthesis at said location and extending therefrom and being free for unconstructed lateral flexure between said location and said side of said tooth to provide for resilient lateral displacement in said clasp.

2. A flexible clasp as defined in claim 1 wherein
said arm is coupled to said prosthesis by resiliently displaceable coupling means; and
said arm engages said side of said tooth below the survey line.

3. A flexible clasp is defined in claim 2 wherein,
said resiliently displaceable coupling means is provided by a resiliently displaceable tubular member mounted on said arm, and clip means mounted to said prosthesis and encircling said tubular member.

4. A flexible clasp as defined in claim 3 wherein,
said arm extends away from said abutment tooth on a side of said clip means remote of said abutment tooth, and said arm is secured to said prosthesis on the remote side of said clip means.

5. A flexible clasp as defined in claim 1 wherein,
the portion of said arm engaging said abutment tooth is formed with a circular cross-section.

6. A laterally flexible, stress relieving clasp including a pair of retention arms formed to engage and extend around at least a portion of opposite sides of said abutment tooth to grip said abutment tooth, said retention arms being further formed to be resiliently laterally displaceable with respect to said sides of said abutment tooth during mounting of said clasp to and removal of said clasp from said abutment tooth, wherein the improvement in said clasp is comprised of:
at least one of said retention arms is is coupled to a dental prosthesis at a location relatively spaced apart from said abutment tooth, and said one of said retention arms is unconstrained against lateral displacement between said location and said abutment tooth; and
a resiliently displaceable element mounted to said one of said arms, said one of said arms and said element being formed for cooperated resilient coupling of said one of said arms to said prosthesis to provide for the lateral displacement required for mounting and removal of said prosthesis and to provide stress relieving connection between said prosthesis and said abutment tooth.

7. A laterally flexible, stress relieving clasp as defined in claim 6 wherein,
said arm extends from said abutment tooth into said edentulous space and is coupled to said prosthesis and the remainder of said clasp at a distance at least about equal to one tooth width from said abutment tooth; and said arm engages said abutment tooth below the survey line thereof.

8. A laterally flexible, stress relieving clasp as defined in claim 7 wherein,
said resiliently displaceable element is provided by a resiliently displaceable tubular member mounted concentrically on said arm, and
said arm and element are resiliently coupled to said prosthesis by clip means mounted to said prosthesis and extending concentrically around said tubular member.

9. A method of forming a stress relieving removable partial dental prosthesis including the step of flexibly connecting a dental prosthesis to clasp means having a pair of opposed arms formed to engage opposite sides of an abutment tooth for retention of said prosthesis thereon, wherein the improvement in said method is comprised of:
said flexibly connecting step being accomplished by coupling said prosthesis to said clasp means through one of said arms by cantilevering said arm from said prosthesis at a spaced distance from said abutment tooth to provide resilient displaceability of said arm to provide both a retention function and a stress relieving function.

10. A method of forming a resiliently displaceable connection of a removable partial dental prosthesis to clasp means having a pair of opposed tooth engaging arms including the step of connecting a dental prosthesis to said clasp means by a resiliently displaceable connection, wherein the improvement in said method is comprised of:
said connecting step being accomplished by coupling said one of said arms of said clasp means directly to said prosthesis at a location spaced apart from said clasp means to provide both unconstrained lateral deflection of said one of said arms and a stress relieving resilient displacement of said prosthesis relative to said clasp means.

* * * * *

UNITED STATES PATENT AND TRADEMARK OFFICE
CERTIFICATE OF CORRECTION

PATENT NO. : 4,483,677
DATED : November 20, 1984
INVENTOR(S) : Leonard J. Kulwiec and Michael F.X. Kulwiec It is certified that error appears in the above-identified patent and that said Letters Patent are hereby corrected as shown below:

Claim 1:

Col. 7, lines 6 and 7, delete "unconstructed" and insert

---unconstrained---.

Signed and Sealed this

Second Day of April 1985

[SEAL]

Attest:

DONALD J. QUIGG

Attesting Officer        Acting Commissioner of Patents and Trademarks